US006555143B2

(12) United States Patent
Miller et al.

(10) Patent No.: US 6,555,143 B2
(45) Date of Patent: Apr. 29, 2003

(54) LEGUME PRODUCTS

(75) Inventors: Jonathan D. Miller, Lawrenceville, NJ (US); Jue-Chen Liu, Belle Mead, NJ (US); Claude Saliou, Gladstone, NJ (US); Miri Seiberg, Princeton, NJ (US); Jeffrey M. Wu, Warrington, PA (US)

(73) Assignee: Johnson & Johnson Consumer Products, Inc., Skillman, NJ (US)

( * ) Notice: Subject to any disclaimer, the term of this patent is extended or adjusted under 35 U.S.C. 154(b) by 0 days.

(21) Appl. No.: 09/796,293

(22) Filed: Feb. 28, 2001

(65) Prior Publication Data
US 2002/0160063 A1 Oct. 31, 2002

(51) Int. Cl.$^7$ .............................................. A61K 35/78
(52) U.S. Cl. ...................................................... 424/757
(58) Field of Search ................................ 424/757, 725; 426/240; 422/22

(56) References Cited

U.S. PATENT DOCUMENTS

| | | |
|---|---|---|
| 3,625,976 A | 12/1971 | Theimer |
| 3,755,560 A | 8/1973 | Dickert |
| 4,007,266 A | 2/1977 | Choay |
| 4,151,304 A | 4/1979 | Evans |
| 4,190,671 A | 2/1980 | Vanstone |
| 4,219,569 A | 8/1980 | Glenn |
| 4,223,018 A | 9/1980 | Belle |
| 4,254,105 A | 3/1981 | Fukuda |
| 4,272,544 A | 6/1981 | Cella |
| 4,278,570 A | 7/1981 | Flom |
| 4,279,930 A | 7/1981 | Hall |
| 4,297,348 A | 10/1981 | Frazier |
| 4,331,692 A | 5/1982 | Drevici |
| 4,333,927 A | 6/1982 | Ofuchi |
| 4,368,187 A | 1/1983 | Flom |
| 4,370,315 A | 1/1983 | Greff |
| 4,382,960 A | 5/1983 | Flom |
| 4,386,067 A | 5/1983 | Guillon |
| 4,421,769 A | 12/1983 | Dixon |
| 4,427,670 A | 1/1984 | Ofuchi |
| 4,437,895 A | 3/1984 | Koulbanis |
| 4,439,418 A | 3/1984 | Moller |
| 4,462,981 A | 7/1984 | Smith |
| 4,486,448 A | 12/1984 | Ser |
| 4,488,564 A | 12/1984 | Grollier |
| 4,515,778 A | 5/1985 | Kastell |
| 4,524,067 A | 6/1985 | Arichi |
| 4,537,782 A | 8/1985 | Millet |
| 4,550,035 A | 10/1985 | Smith |
| 4,578,267 A | 3/1986 | Salamone |
| 4,584,190 A | 4/1986 | Tejima |
| 4,604,281 A | 8/1986 | Deckner |
| 4,612,192 A | 9/1986 | Scheuffgen |
| 4,690,821 A | 9/1987 | Smith |
| 4,707,293 A | 11/1987 | Ferro |
| 4,760,096 A | 7/1988 | Sakai |
| 4,793,991 A | 12/1988 | Slimak |
| 4,824,662 A | 4/1989 | Hofmann |
| 4,834,076 A | 5/1989 | Millet |
| 4,847,267 A | 7/1989 | Deckner |
| 4,851,214 A | 7/1989 | Walters |
| 4,859,458 A | 8/1989 | Salamone |
| 4,867,964 A | 9/1989 | Forestier |
| 4,871,530 A | 10/1989 | Grollier |
| 4,885,169 A | 12/1989 | Gazzani |
| 4,895,839 A | 1/1990 | Bombardelli |
| 4,906,457 A | 3/1990 | Ryan |
| 4,943,462 A | 7/1990 | Komerska |
| 4,960,588 A | 10/1990 | Hoshowski |
| 4,960,764 A | 10/1990 | Figueroa |
| 4,970,216 A | 11/1990 | Deckner |
| 4,971,825 A | 11/1990 | Kitazume et al. |
| 5,002,761 A | 3/1991 | Mueller |
| 5,032,382 A | 7/1991 | Crollie |
| 5,032,400 A | 7/1991 | Wiersum |
| 5,043,323 A | 8/1991 | Bombardelli |
| 5,077,038 A | 12/1991 | Hofmann |
| 5,077,040 A | 12/1991 | Bergmann |
| 5,104,655 A | 4/1992 | Bombardelli |
| 5,110,603 A | 5/1992 | Rau |
| 5,116,605 A | 5/1992 | Alt |
| 5,118,671 A | 6/1992 | Bombardelli |
| 5,147,859 A | 9/1992 | Bombardelli |
| 5,166,139 A | 11/1992 | Bombardelli |
| 5,171,577 A | 12/1992 | Griat |
| 5,179,091 A | 1/1993 | Lesieur |
| 5,188,823 A | 2/1993 | Shapiro |
| 5,192,332 A | 3/1993 | Lang |

(List continued on next page.)

FOREIGN PATENT DOCUMENTS

| | | |
|---|---|---|
| EP | 0421021 | 6/1989 |
| EP | 0473502 A1 | 3/1992 |
| EP | 0273202 B1 | 6/1995 |

(List continued on next page.)

OTHER PUBLICATIONS

Lam et al. 7th Symp. on Radiation Chemistry (1990); 477–83. Combined effect of irradiation and dielectric heating on chemical properties of soybeans.*

Kovacs et al. Food Structure (1991); 10: 217–227. Effect of irradiation and dielectric heating on soybean ultrastructure, trypsin inhibitor, and lipoxygenase activities.*

Badash et al. Chemie Mikrobiologie Technologie der Lebensmittel (1992); Badash et al. Effect of gamma irradiation of field and storage fungi of wheat, maize and soybean.*

(List continued on next page.)

Primary Examiner—Christopher R. Tate
Assistant Examiner—Michele C. Flood
(74) Attorney, Agent, or Firm—William E. McGowan

(57) ABSTRACT

The present invention features legume products having trypsin inhibitory activity and reduced microbial content, methods of decontaminating such legume products, compositions containing such legume products, and the topical application of such legume products or compositions to skin, nails, and hair.

25 Claims, No Drawings

U.S. PATENT DOCUMENTS

| | | | |
|---|---|---|---|
| 5,194,252 | A | 3/1993 | Hofmann |
| 5,217,717 | A | 6/1993 | Kennedy |
| 5,229,104 | A | 7/1993 | Sottery |
| 5,231,090 | A | 7/1993 | Hsia |
| 5,248,495 | A | 9/1993 | Patterson |
| 5,254,331 | A | 10/1993 | Mausner |
| 5,260,065 | A | 11/1993 | Mathur |
| 5,270,042 | A | 12/1993 | Whitham |
| 5,276,058 | A | 1/1994 | Satoh |
| 5,306,444 | A | 4/1994 | Kitamura |
| 5,310,734 | A | 5/1994 | Losch |
| 5,322,839 | A | 6/1994 | Voegeli |
| 5,352,443 | A | 10/1994 | Kubo |
| 5,362,494 | A | 11/1994 | Zysman |
| 5,364,886 | A | 11/1994 | Loliger |
| 5,393,519 | A | 2/1995 | Dowell |
| 5,397,497 | A | 3/1995 | Jakobson |
| 5,407,675 | A | 4/1995 | Etemad-Moghadam |
| 5,411,742 | A | 5/1995 | Sebag |
| 5,427,814 | A | 6/1995 | Loliger |
| 5,428,026 | A | 6/1995 | Colarow |
| 5,438,044 | A | 8/1995 | Losch |
| 5,439,672 | A | 8/1995 | Zabotto |
| 5,443,839 | A | 8/1995 | Meybeck |
| 5,443,840 | A | 8/1995 | Morancais |
| 5,446,605 | A | 8/1995 | Umehara |
| 5,466,452 | A | 11/1995 | Whittle |
| 5,498,420 | A | 3/1996 | Edgar |
| 5,510,391 | A | 4/1996 | Elson |
| 5,523,308 | A | 6/1996 | Costanzo |
| 5,539,129 | A | 7/1996 | Zysman |
| 5,545,399 | A | 8/1996 | Lee |
| 5,547,661 | A | 8/1996 | Sun |
| 5,554,647 | A | 9/1996 | Perricone |
| 5,567,420 | A | 10/1996 | McEleney |
| 5,569,663 | A | 10/1996 | Ribier |
| 5,571,503 | A | 11/1996 | Mausner |
| 5,578,297 | A | 11/1996 | Mellul |
| 5,589,181 | A | 12/1996 | Bencsits |
| 5,595,984 | A | 1/1997 | Blank |
| 5,597,814 | A | 1/1997 | Blank |
| 5,601,833 | A | 2/1997 | Roboer |
| 5,603,949 | A | 2/1997 | Meybeck |
| 5,605,894 | A | 2/1997 | Blank |
| 5,607,666 | A | 3/1997 | Masson |
| 5,607,692 | A | 3/1997 | Ribier |
| 5,614,180 | A | 3/1997 | Chung |
| 5,614,215 | A | 3/1997 | Ribier |
| 5,616,572 | A | 4/1997 | Blank |
| 5,618,522 | A | 4/1997 | Kaleta |
| 5,620,692 | A | 4/1997 | Potter |
| 5,622,690 | A | 4/1997 | Potter |
| 5,626,868 | A | 5/1997 | Morancais |
| 5,629,015 | A | 5/1997 | Ribier |
| 5,629,301 | A | 5/1997 | Blank |
| 5,631,318 | A | 5/1997 | Ito |
| 5,635,165 | A | 6/1997 | Panitch |
| 5,637,316 | A | 6/1997 | Ribier |
| 5,639,785 | A | 6/1997 | Kung |
| 5,641,509 | A | 6/1997 | Gross |
| 5,643,583 | A | 7/1997 | Voultoury |
| 5,643,587 | A | 7/1997 | Scancarella |
| 5,643,601 | A | 7/1997 | Gross |
| 5,650,166 | A | 7/1997 | Ribier |
| 5,652,230 | A | 7/1997 | Blank |
| 5,653,988 | A | 8/1997 | Gerber |
| 5,660,853 | A | 8/1997 | Hansenne-Richoux |
| 5,665,367 | A | 9/1997 | Burger |
| 5,674,511 | A | 10/1997 | Kacher |
| 5,676,935 | A | 10/1997 | Mellul |
| 5,676,956 | A | 10/1997 | Duffy |
| 5,679,374 | A | 10/1997 | Fanchon |
| 5,681,852 | A | 10/1997 | Bissett |
| 5,683,683 | A | 11/1997 | Scafidi |
| 5,686,102 | A | 11/1997 | Gross |
| 5,691,327 | A | 11/1997 | Blank |
| 5,723,148 | A | 3/1998 | Love |
| 5,741,496 | A | 4/1998 | Khaiat |
| 5,753,612 | A | 5/1998 | Mitrani |
| 5,755,814 | A | 5/1998 | Berg |
| 5,762,916 | A | 6/1998 | Ansmann |
| 5,766,628 | A | 6/1998 | Nurnberg |
| 5,776,917 | A | 7/1998 | Blank |
| 5,780,456 | A | 7/1998 | Blank |
| 5,780,457 | A | 7/1998 | Blank |
| 5,780,458 | A | 7/1998 | Blank |
| 5,780,459 | A | 7/1998 | Blank |
| 5,786,345 | A | 7/1998 | Blank |
| 5,786,346 | A | 7/1998 | Blank |
| 5,789,396 | A | 8/1998 | Blank |
| 5,795,879 | A | 8/1998 | Blank |
| 5,801,163 | A | 9/1998 | Blank |
| 5,804,216 | A | 9/1998 | Terren |
| 5,807,545 | A | 9/1998 | Coffindaffer |
| 5,824,702 | A | 10/1998 | Wei |
| 5,833,965 | A | 11/1998 | Sun |
| 5,834,013 | A | 11/1998 | Ribier |
| 5,840,717 | A | 11/1998 | Blank |
| 5,843,926 | A | 12/1998 | Blank |
| 5,863,546 | A | 1/1999 | Swinehart |
| 5,869,470 | A | 2/1999 | Blank |
| 5,871,743 | A | 2/1999 | Chajuss |
| 5,880,314 | A | 3/1999 | Shinomiya |
| 5,885,593 | A | 3/1999 | Epstein |
| 5,885,596 | A | 3/1999 | Parab |
| 5,885,600 | A | 3/1999 | Blum |
| 5,885,617 | A | 3/1999 | Jordan |
| 5,885,948 | A | 3/1999 | Glenn |
| 5,908,618 | A | 6/1999 | Lorant |
| 5,912,175 | A | 6/1999 | Wille, Jr. |
| 5,916,577 | A | 6/1999 | Golz |
| 5,928,654 | A | 7/1999 | Duranton |
| 5,928,658 | A | 7/1999 | Kishida |
| 5,928,889 | A | 7/1999 | Bakich |
| 5,942,479 | A | 8/1999 | Frankenback |
| 5,945,095 | A | 8/1999 | Mougin |
| 5,945,109 | A | 8/1999 | Schmidt |
| 5,952,373 | A | 9/1999 | Lanzendorfer |
| 5,958,387 | A | 9/1999 | Bara |
| 5,961,980 | A | 10/1999 | Kennedy |
| 5,962,015 | A | 10/1999 | Delrieu |
| 5,962,441 | A | 10/1999 | Blank |
| 5,965,153 | A | 10/1999 | Allen |
| 5,981,450 | A | 11/1999 | Fabry |
| 5,985,338 | A | 11/1999 | Suh |
| 5,985,809 | A | 11/1999 | Frankenback |
| 5,990,291 | A | 11/1999 | Waggle |
| 6,004,915 | A | 12/1999 | Elliott |
| 6,013,250 | A | 1/2000 | Cannell |
| 6,013,255 | A | 1/2000 | Edens |
| 6,017,893 | A | 1/2000 | Segelman |
| 6,019,962 | A | 2/2000 | Rabe |
| 6,030,931 | A | 2/2000 | Vinski |
| 6,033,680 | A | 3/2000 | Dixon |
| 6,045,779 | A | 4/2000 | Mueller |
| 6,048,520 | A | 4/2000 | Hoshowski |
| 6,051,602 | A | 4/2000 | Bissett |
| 6,054,137 | A | 4/2000 | Breton |
| 6,060,070 | A | 5/2000 | Gorbach |
| 6,063,398 | A | 5/2000 | Gueret |
| 6,093,411 | A | 7/2000 | Bissett |

| | | | |
|---|---|---|---|
| 6,180,662 B1 | 1/2001 | Lanzendorfer | |
| 6,183,761 B1 | 2/2001 | Bissett | |
| 6,261,603 B1 | 7/2001 | McElwain | |
| 6,323,219 B1 | 11/2001 | Costanzo | |

FOREIGN PATENT DOCUMENTS

| | | | |
|---|---|---|---|
| EP | 0707851 A2 | 4/1996 | |
| EP | 0774249 A2 | 5/1997 | |
| EP | 0811595 A1 | 12/1997 | |
| EP | 0707851 A3 | 4/1998 | |
| EP | 1074240 A2 | 2/2001 | |
| EP | 1077063 A2 | 2/2001 | |
| JP | 6-2036304 A | 2/1967 | |
| JP | 58-225003 | 6/1982 | |
| JP | 59187756 | * 10/1984 | |
| JP | 63-68512 | 9/1986 | |
| JP | 63-316711 | 6/1987 | |
| JP | 196106 | 10/1987 | |
| JP | 63-96120 | 4/1988 | |
| JP | 63-227515 | 9/1988 | |
| JP | 3-127713 | 10/1989 | |
| JP | 5-320061 | 5/1991 | |
| JP | 5-320024 | 5/1992 | |
| JP | 4-169514 | 6/1992 | |
| JP | 5-213729 | 8/1993 | |
| JP | 5-246932 | 9/1993 | |
| JP | 899891 | 1/1994 | |
| JP | 7304655 | 5/1994 | |
| JP | 812560 | 6/1994 | |
| JP | 8020597 | 7/1994 | |
| JP | 925212 | 7/1995 | |
| JP | 925214 | 7/1995 | |
| JP | 11346695 | * 12/1999 | |
| KR | 92-8851 | 10/1992 | |
| RU | 2066992 | 9/1996 | |
| WO | WO 91/07166 | 5/1991 | |
| WO | WO 95/24885 A1 | 9/1995 | |
| WO | WO 96/09806 A2 | 4/1996 | |
| WO | WO 96/19483 | 6/1996 | |
| WO | WO 96/19491 | 6/1996 | |
| WO | WO 96/24371 | 8/1996 | |
| WO | WO 96/30035 | 10/1996 | |
| WO | WO 96/30396 | 10/1996 | |
| WO | WO 96/31194 | 10/1996 | |
| WO | WO 96/37497 | 11/1996 | |
| WO | WO 97/11033 | 3/1997 | |
| WO | WO 97/35998 | 10/1997 | |
| WO | WO 97/39733 A1 | 10/1997 | |
| WO | WO 98/02134 | 1/1998 | |
| WO | WO 98/05333 | 2/1998 | |
| WO | WO 98/08503 | 3/1998 | |
| WO | WO 98/09987 | 3/1998 | |
| WO | WO 98/49153 | 11/1998 | |
| WO | WO 99/04752 A2 | 2/1999 | |
| WO | WO 99/24003 | 5/1999 | |
| WO | WO 99/30729 A1 | 6/1999 | |
| WO | WO 99/36050 | 7/1999 | |
| WO | WO 00/15188 | 3/2000 | |
| WO | WO 00/43049 | * 7/2000 | |
| WO | WO 00/51554 | 9/2000 | |
| WO | WO 00/62740 | 10/2000 | |
| WO | WO 00/62741 | 10/2000 | |
| WO | WO 00/62743 | 10/2000 | |
| WO | WO 00/62744 | 10/2000 | |
| WO | WO 00/62745 | 10/2000 | |
| WO | WO 00/69404 | 11/2000 | |
| WO | WO 00/69406 | 11/2000 | |
| WO | WO 00/69407 | 11/2000 | |
| WO | WO 00/69408 | 11/2000 | |
| WO | WO 02/07697 A1 | 1/2002 | |

OTHER PUBLICATIONS

Hattori et al. Food Irradiation (1968); 3(1): 104–110. Effects of .sup.6.sup.O Co. –gamma–rays on defatted soybean powder.*

Tech Times (1978), pp. 10. A combined soybean crushing–deodorizing system that yields 100–200 mesh powder for food additive use has been developed by Shinyu Zoki Co Ltd and Mitsubishi Rayon Engineering Ltd.*

Adhesion Molecule Expression in Normal Skin and Melanocytic Lesions. Tronnier, Michael, et al. Journal of Cutaneous Pathology, 1997, pp. 278–285.

Altered Cell Signaling and Mononuclear Phagocyte Deactivation during Interacellular Infection. Reiner, Neil E. Immunology Today. 1994. pp. 374–381.

A Growth–regulated Protease Activity That is Inhibited by the Anticarcinogenic Bowen–Birk Protease Inhibitor, Billings et al., Pro. Natl. Acad. Sci. 89:3120–3124 (1992).

Amino Acid Sequence and Secondary Structural Analysis of the Corn Inhibitor of Trypsin and Activated Hageman Factor, Walter C. Mahoney:: Journal of Biological Chemistry, vol. 259, No. 13 Jul. 10, 1984, 8412–8416.

Amino Acid Sequences of Double–headed Proteinase Inhibitors from the Seeds of *Canavalia lineata*, Shigeyuki Terada: Biosci. Biotech. Biochem. vol. 58, (2), 376–379 (1994).

A Serine Protease From Suspension–Cultured soybean Cells, Ze–Jian Guo: Phytochemistry, vol. 47, No. 4 (1998) 547–553.

Astrocytes Regulate Microglial Phagocytosis of Senile Plaque Cores of Alzheimer's Disease. DeWitt, David A., Institute of Pathology, 1998 pp. 329–340.

Aqueous Ethanol Extraction of Soybean Trypsin Inhibitors and Characterization of a Calcium–Sensitive: Keshun Liu, Journal Of Food Biochemistry 15(1991) 159–168.

Cardiovascular and Renal Small molecule direct thrombin inhibitors, Wiley and Fisher, Ashley Publications, Ltd., 1997, pp. 1265–1282.

Chemistry and Nutritional value of soybean components. In: Soybeans, chemistry, technology and utilization. Liu, K., pp. 32–35 (Aspen publishers, Inc., Gaithersburg, MD, 1999).

Correlation Between Endogenous Glutathione R.M. Tyrrell and M. Pidoux, Photochem. Photobiol. 47:405–412 (1988).

Cosmetics, Science and Technology, 2nd Edition, Sagarin, vol. 1, pp. 32–43 (1972).

Cosmetics, Science and Technology, 2nd Edition, Sagarin, vol. 1, pp. 72–73 (1972).

Common Disorders of Pigmentation. Hacker, Steven M., Postgraduate Medicine. 1996, pp. 177–186.

Cell–Marix Interactions in the Genesis of Arteriosclerosis and Alateroma (Effect of Aging). Robert, L., et al. Laboratorie de Biologie du Tissu Conjonctif 1992, pp. 331–341.

"Chemopreventive Agents: Protease Inhibitors," Ann R. Kennedy, Department of Radiation Oncology, University of PA School of Medicine, Philadelphia, PA 19104, USA Pharmacol. Ther. 78(3):167–209, 1998, Copyright 1998 Elsevier Science Inc.

Current Protocols in Cell Biology, Edited by Juan S. Bonifacino et al. Chapter 6: Electrophoresis and Immunoblotting. Copyright 1999 by John Wiley & Sons, Inc.

Defining Food Components as New Nutrients, Suzanne Hendrick: American Institute of Nutrition (1994) 1789S–1792S.

Depletion of Cutaneous Glutathione By Ultraviolet Radiation M.J. Connor and L.A. Wheeler, Photochem. Photobiol. 46:239–246 (1987).

Differential Regulation of Human Keratinocyte Growth and Differentiation by a Novel Family of Protease–activated Receptors, Claudia Derian; Cell Growth & Differentiation vol. 8, 743–749, Jul. 1997.

Diazepam Inhibits Phagocytosis and Killing Exerted by Polymorphonuclear Cells and Monocytes from Healthy Donors. Abstract. Immunopharmacology and Immunotoxicology (1989) pp. 701–714.

Do Microglial Cells Phagocyte the B/A4–Amyloid Senile Plaque Core of Alzheimer Diesease? Hachimi, K. et al., Academy of Science, Paris. 1994, pp. 445–451.

Effect of Heat Treatments on Trypsin/Chyomotrypsin Inhibitor Activity of Red Gram (Cajanus Cajan L.), V.H. Mulimani: Plant Foods for Human Nutrition, vol. 46, No. 2, (1994) 103–107.

Effects of heat treatment and germination on trypsin and chymotrypsin inhibitory activities in sorghum (*Sorghum bicolor* (L.) Moench) seeds, V.H. Mulimani: Plant Foods for Human Nutrition, vol. 44, No. 3 (1993) 221–226.

Evaluation of the Effects of Hair Re–growth Agents on Lengthening the Anagen Phase Period and Blockade of Anagen phase–Catagen phase Transformation, Kazuto, J. Soc. Cosmet. Chem Japan, vol. 31 No.4(1997):413–419.

Fluorescence assay to Monitor Phagocytosis by Blood–Clot Derived Polymorphonuclear Leucocytes Study of Patients with Diabetes and Phagocytosis of Different Staphyloccoccal Species. Muxclow, C. Elizabeth et al., Mount Sinai Hospital, 1991, pp. 15–24.

"Evidence for the Presence of a Protease–Activated Receptor Distinct from the Thrombin Receptor in Human Keratinocytes" R.J. Santulli et al. Proceeding of the National Academy of Sciences of USA, vol. 92, Sep. 1995, pp. 9151–9155.

Glutathione, Ascorbate, and Cellular Protection A. Meister, Cancer Res. 54:1969s–1975s (1994).

"Glucocorticoid Effect on Hair Growth Initiation: A Reconsideration," Stenn, et al., 6 Skin Pharmacol., 125–134 (1993).

Handbook of Non–Invasive Methods and the Skin, eds. J. Serup & G. Jemec, Chapter 14.3 (1995).

High–Performance Liquid Chromatographic Analysis of Phytoestrogens in Soy Protein Preparations with Ultraviolet Electrochemical and Thermospray Mass spectrometric Detection, K.D. R. Setchell: Journal of Chromotography 386 (1987) 315–323.

Immunologic Aspects of Lung Diseases and Cystic Fibrosis. Greenberger, Paul A. Jama, 1997, pp. 1924–1930.

"Interactions of Mast Cell Tryptase with Thrombin Receptors and PAR–2" M. Molino et al. Journal of Biological Chemistry, vol. 272, No. 7, Feb. 14, 1997 pp. 4043–4049.

Isolation and Properties of Anionic Protease Inhibitors from Buckwheat Seeds, Y.E. Dunaevsky: Biochemistry and Molecular Biology International, vol. 40, No. 1, (1996) 199–208.

Intercellular Adhesion Molecule–1. Van de Stope, A., et al. University Hospital Nijmegen, The Netherlands. 1996 pp. 13–33.

Influence of Nonionic Liposomal Composition on Topical Delivery of Peptide Drugs into Pilosebaceous Units:An in Vivo Study Using the Hamster Ear Model: Pharmaceutical Research, vol. 12, No. 8, 1995 p. 1184–1188.

"Inhaled Tryptase Causes Bronchoconstriction in Sheep Via Histamine Release" Jussara F. Molinari, Mario Scuri, William R. Moore, James Clark, Richard Tanaka, and William M. Abraham, Division of Pulmonary Disease, University of Miami at Mount Sinai Medical Center, Miami Beach, Florida and the Arris Pharmaceutical Corporation, South San Francisco, CA, , am J Respir Crit Care Med vol. 154 pp. 649–653, 1996.

Inhibition of Serine Proteases of the Blood Coagulation System by Squash Family Protease Inhibitors, Kaeko Hayaski: J. Biochem. 116, 1013–1018 (1994).

Interaction of Proteases with Legume Seed Inhibitors. Molecular features, Dinah S. deSeidl: Archivos Latinoamericanos de Nutricion, vol. 44 No. 4–S (1994) 21–S–25–S.

Inflammatory and immune responses are impaired in mice deficient in intercellular adhesion molecule I. Sligh, James E., et al. Proc. Natl. Acad., Sci. 1993, pp. 8529–8533.

Identification Of Potential Activators Of Proteinase–Activated Receptor–2. Fox, Mark T., et al. Federation of European Biochemical Societies. 1997. Pp. 267–269.

Kunitz–Type Soybean Trypsin Inhibitor Revisited,Song et al., J. Mol. Biol. 275:347–63 (1998).

"Liposomes—A Selective Drug Delivery System for the Topical Route Of Administration; Gel Dosage Form", Mezei & Gulasekharam Journal of Pharmaceutics and Pharmacology, vol. 34 (1982), pp. 473–474.

"Liposomes as a Skin Drug Delivery Systems", Topics in Pharmaceutical Sciences Mezei, M., (D. D. Breimer and P. Speiser, eds.,), Elsevier Science Publishers B. V., New York, N.Y., 1985, pp. 345–358.

Leukocytosis, Monocytosis and Neutrophilla; Hallmarks of Severe Depression. Maes, M., et al. J. Psychiat. Res. 1992, pp. 125–134.

Mammalian tyrosinase: biosynthesis, processing and modulation by melanocyte stimulating hormone. Jimenez, M., Kameyama, K., Maloy, WL, Tomita Y., and Hearing, V. Proc. Natl. Acad. Sci. USA (1988), 85:3830–3834.

McCutcheon's Detergents and Emulsifiers, North American Edition, pp. 317–324 (1986).

Macrophage Uptake of Cholesterol–Containing Particles Derived from LDL and Isolated from Atherosclerotic Lesions. Hoff, H.F., et al. European Heart Jouenal, 1990, pp. 105–115.

Mid–Dermal Elastolysis; An Ultrastructural and Biochemical Study. Fimiani, M., et al., Siena University, 1995, pp.152–157.

Neutrophil and Monocyte Phagocytosis In Depressed Patients. McAdams C., et al. Neuro–Psychopharmacol & Bio. Psychiat, 1998 pp. 971–984.

Nutrition Communique Soy: Just a Hill of Beans? Clare M. Hasler: Journal of women's Health, vol. 7, No. 5 (1998) 519–523.

Grant–Theule, D. Periodontal Disease, Diabetes, and Immune Response; A Review of Current Concepts, Periodontal Abstracts, vol. 44, No. 3, 1996:69–77.

Partial Purification and Characterization of a Novel Soybean Protease Which is Inhibited by Kunitz and Bowman–Birk Trypsin Inhibitors, Shimpei Morita, vol. 119, No. 4, 1996 p. 711–718.

Photocarcinogenesis and Inhibition of Intercellular Adhesion Molecular I Expression In Cells Of DNA–Repair–Defective Individuals. Ahrens, C., et al. The National Academy of Sciences 1997, pp. 6837–6841.

Phytoestrogen Content of Processed Soybean Products, P.A. Murphy: Food Technology, vol. 1, 60–64 (1982).

Preservation of Cosmetics, F. Sharpell Chapter 51, p. 887–900, publicly available prior to Feb. 28, 2001.

Potent Thrombin Inhibitors That Probe the S Subsite: Tripeptide Transition State Analogues Based On A Heterocycle Activated Carbonyl Grup. Costanzo, Michael j., et al. J. Med. Chem. 1996, pp. 3039–3043.

Protease–Activated G Protein Coupled Receptors On Human Platelets and Endothelial Cells. Brass, Lawrence F., et al. University of Pennsylvania, 1997, pp. 234–241.

Protease Activated Receptors Start A Family. Couglin, shaun R., University of California, 1994, pp. 9200–9202.

Primary Structure of a Kunitz–Type Trypsin Inhibitor From Enterolobium Contortisiliquum Seeds, I.F.C. Batista: Phytochemistry vol. 41, No. 4, (1996) 1017–1022.

Protection Against UV–Induced Reactivr Intermediate, D. P. T. Steenvoorden, et al., Photochem Photobiol. 67:651–656 (1998).

Photoprotective Effect of Esterfied Glutathione Against Ultraviolet B–Induced Sunburn Cell K. Hanada, et al., J. Invest. Dermatol. 108:727–730 (1997).

Protein Proteinase inhibitors in legume seeds—Overview, Yehudith Birk: Archivos Latinoamericanos de Nutricion, vol. 44, No. 4–S (1994) 26–S–30–S.

Refractory Periodontitis Associated with Abnormal Polymorphonuclear Leukocyte Phagocytosis and Cigarette Smoking. J. Peridontal, Nov. 1992, MacFarlane, Gordon, et al. University of Minneapolis, pp. 908–913.

"Single–Step Method of RNA Isolation by Acid Guanidinium Thiocyanate–Phenol–Chloroform Extraction," Piotr Chomczynski & Nicoletta Sacchi, Analytical Biochemistry 162, 156–159 (1987), Copyright 1987 by Academic Press, Inc.

Soy Intake and Cancer Risk: A Review of the InVitro and InVivo Data, Mark J. Messina: Nutrician and Cancer vol. 21, No. 2, (1994) 113–131.

Specific Identification of an authentic tyrosinase clone. Jimenez, M., K., Maloy, WL, and Hearing, V. J. Biol. Chem. (1989) 264:3397–3403.

Subcellular Distribution of Tyrosinase and Tyrosinase–Related Protein–L;Implications for Melanosomal Biogenesis. Orlow, Seth J., et al. The Socieity for Investigative Dermatology, Inc. 1993, pp. 55–64.

The Complete Amino Acid Sequence of Rice Bran Trypsin Inhibitor: J. Biochem 102, 2970–306 (1987).

The biochemistry and nutrition group:30 years of research in a developing country, Abraham Levy Benshimol: Archivos LatinoAmericanos De Nutrician, vol. 44, No. 4–S, pp 5–S–9–S (1994).

"The Bowman–Birk Inhibitor", Int. J. Pept. Protein Res. 25:113–131 (1985).

The Bowman Birk Inhibitor from Soybeans As An Anticarcinogenic Agent), Kennedy, Am. J. Clin. Neutr. 68:1406S–1412S (1998).

The Effect of a Drug–delivery System Consisting of Soybean Phosphatidyl Choline and Medium–chain Monoacylglycerol on the Intestinal Permeability of Hexarelin in the Rat, Urban Fagerholm: J. Pharm. Pharmacol (1998) 50: 467–473.

The Role of Proteolytic Enzymes in the Development of Pumonary Emphysema and Periodontal Disease. Travis, J., et al. University of Georgia and Institute of Molecular Biology. 1994, pp. S143–S146.

The Role Of Neutrophil Elastase in Chronic Inflammation. Doring, Grd. Department of Genreal Hygience and Enviromental Hygiene, 1994, pp. 114–117.

The Use of Endogenous Antioxidants to Improve Photoprotection Steenvoorden et al., Journal of Photochemistry and Photobiology B:Biology 41 (1997) 1–10.

The Use of Thermospray Liquid Chromatography/Tandem Mass spectrometry for the Class Identification and Structural Verification of Phytoestrogens in Soy Protein Preparations, Robert J. Barbuch: Biomedical and Enviromental Mass Spectrometry, vol. 18, (1989) 973–977.

Tryptase Inhibitors Block Allergen–induced Airway and Inflammatory Responses in Allergic Sheep, Warne, William R. Moore, and Richard D. Tanaka, Dept of Molecular Pharmacology, Inflammation Program, Arris Pharmaceutical Corp, Souch San Francisco, CA, and Department of Research, Division of Pulmonary Diseases, University of Miami at Mount Sinai Medical Center, Miami Beach, Florida, Am J Respir Crit Care Med vol. 152. pp 2076–2083, 1995.

Trypsin Inhibitor Polymorphism: Multigene Family Expression and Posttranslational Modification, Laurence Quillien: Journal of Protein Chemistry, vol. 16, No. 3 (1997) 195–203.

Trypsin Inhibitor Activity in Commercial Soybean Products in Japan, Yuko Miyagi: J. Nutr. Sci. Vitaminol (1997) vol. 43: 575–580.

Two Groups of Protease Inhibitors Functionally Active in Buckwheat Seeds, Yakov Dunaevsky:soba.shinshu–uac.jp/contents/105.html, publicly available prior to Feb. 28, 2001.

Wheat Germ Trypsin Inhiboors. Isolation and Structural Characterization of Single–Headed and Double–Headed Inhibitors of the Bowman–Birk Type: J. Biochem 100, 975–983 (1986).

"RQ1 RNase–Free DNASE, Promega," Technical Bulletin No. 518, pp. 1–4, Feb. 2000, Promega Corporation, 2800 Woods Hollow Rd, Madison, WI 53711–5399.

"Invitrogen Life Technologies, ThermoScript RNase H–Reverse Transcriptase," www.invitrogen.com/content.cfm, Invitrogen Corporation, 2001.

Leaflet from Ichimaru Pharcos issued Mar. 7, 1997 "Plant Extract Containing Female Hormone–Like Isoflavones".

Thrombin Inhibitors: Relevant Patent Applications as of Jul. 8, 1998 and Oct. 1, 1996.

Concerns Regarding Soybeans: www.rheumatic.org/soy.htm, publicly available prior to Feb. 28, 2001.

Soy Therapy, www.wiseessentials.com/soytherapy.html (Apr. 13, 2000).

Brochure on Lipoxydase Code 411784, Apr. 1999.

Chapter 8: Antithrombotics/Serine Protease; William Ripka and George Vlasuk, Covads International, San Diego, CA, publicly available prior to Feb. 28, 2001.

Helena Rubinstein Whitening with Soybean? HR has launched "Future White" in Japan, publicly available prior to Feb. 28, 2001.

"Isoral" Soybean power makes your skin clear and moist—Brochure, publicly available prior to Feb. 28, 2001.

Elhibin—Brochure, Centerchem, Inc., publicly available prior to Feb. 28, 2001.

Avon's Anew Positivity Trio Targets Menopausal Women, The Rose Sheet, Feb. 28, 2000, p. 8.

Soybean Technology Improves Skin, Allured's Cosmetics & Toiletries Magazine vol. 115, No., 3, Mar. 2000, p. 22.

Nudit—Advertisement, publicly available prior to Feb. 28, 2001.

Anti–regrowth effect of hair, Dec. 22, 1998, pp. 11–13.

"CaspACE Assay System, Colorimetric," Product Improvements, Neural Notes Vol. V, Issue 1 1999, p. 13.

Abstracts of requested patent titles 1996.

Abstract for Product for Damaged hair by Bristol–Myers–Squibb, publicly available prior to Feb. 28, 2001.

Gastric Juice for Antiaging—Abstracts 1997.

Soybeans for skin pigmentation—Abstracts 1997.

Soybeans for skin whitening—Chemical Abstracts 1997.

Plant extracts for skin whitening—Abstracts, publicly available prior to Feb. 28, 2001.

EnzChek™ Protease Assay Kits Product Information, Revised Mar. 15, 1999; Molecular Probes, Eugene OR.

U.S. patent application Ser. No. 09/796,054, Johnson & Jonson Consumer Companies, Inc., J&J–2001, pending.

U.S. patent application Ser. No. 09/795,762, Johnson & Johnson Consumer Companies, Inc., J&J–2002, pending.

U.S. patent application Ser. No. 09/677,511, Johnson & Johnson Consumer Companies, Inc., JBP–523, pending.

U.S. patent application Ser. No. 698,454, Johnson & Johnson Consumer Companies, Inc., JBP–518, pending.

M. Seiberg, S. Wisniewski, G. Cauwenbergh, S. Shapiro, Trypsin–Induced Follicular Apoptosis Results in Delayed Hair Growth and Pigmentation, Developmental Dynamics, (1997) 208:553–564, Wiley–Liss, Inc.

Yu DW, Yang T, Sonoda T, GaffneyK, Jensen PJ, Dooley T, Ledbetter S, Freedberg IM, Lavker R, Sun TT, Message of nexin 1, a serine protease inhibitor, is accumulated in the follicular papilla during anagen of the hair cycle, J. Cell Sci, 1995, abstract.

Xiang M, Yang T, A study of Nexin 1 of skin and hair follicle during postnatal development period of rat, Zhongguo Yi Xue Ke Xue Yuan Xue Bao, Apr. 20, 1998, abstract.

* cited by examiner

LEGUME PRODUCTS

FIELD OF THE INVENTION

The present invention relates to legume products, topical compositions containing such legume products, and the manufacture and use thereof.

BACKGROUND OF THE INVENTION

Legume fruits contain high levels of proteins, lipids and carbohydrates. Consequently, legume fruits, such as soybeans, and compositions containing legume fruits are considered a great nutrient for human use. Legume fruits also contain compounds that inhibit protease activity. For example, two protein protease inhibitors were isolated from soybeans in the early 1940's, the Kunitz-type trypsin inhibitor (soybean trypsin inhibitor, STI) and the Bowman-Birk protease inhibitor (BBI). See, e.g., Birk, Int. J. Pept. Protein Res. 25:113–131 (1985) and Kennedy, Am. J. Clin. Neutr. 68:1406S-1412S (1998).

STI inhibits the proteolytic activity of trypsin by the formation of a stable stoichiometric complex. See, e.g., Liu, K., Chemistry and Nutritional value of soybean components. In: Soybeans, chemistry, technology and utilization. pp. 32–35 (Aspen publishers, Inc., Gaithersburg, Md., 1999). STI consists of 181 amino acid residues with two disulfide bridges and is roughly spherically shaped. See, e.g., Song et al., J. Mol. Biol. 275:347–63 (1998).

BBI is an 8 k-Da protein that inhibits the proteases trypsin and chymotrypsin at separate reactive sites. See, e.g., Billings et al., Pro. Natl. Acad. Sci. 89:3120–3124 (1992). STI and BBI are found only in the soybean seed, and not in any other part of the plant. See, e.g., Birk, Int. J. Pept. Protein Res. 25:113–131 (1985).

However, due to its natural origin, high levels of microorganisms are carried on the outside of legume fruits, such as soybeans. Consequently, decontamination processes such as heat, organic/aqueous solvent extraction, and high shear purification may be used to reduce such microorganism concentrations to allow it to be safe for human use, e.g., skin care applications. Applicants, however, have found that these processes, which frequently denature the active compounds in the soy, result in a compromised biological efficacy (e.g., a reduction in protease inhibitory activity) which is important for cosmetic and therapeutic uses to the skin, hair, and nails. Furthermore, such processes also can lead to instability of the soy product as well as to an undesirable odor and color generation. Therefore, there is a commercial need to develop a means to reduce the levels of microbials in soy products without compromising the biological benefits of such products.

The object of the present invention is to provide for a soy product (e.g., that can be used as an ingredient in a skin, hair, or nail care composition) that has reduced microbial content but maintains its protease inhibitory activity. Another object of the invention is to provided for a skin, hair, or nail care composition containing such soy product optionally with other active agents.

The present invention relates to legume products containing reduced microbial content that retains legume's beneficial biological activities, processes for obtaining such legume products, and uses thereof in cosmetic compositions.

SUMMARY OF THE INVENTION

The present invention features legume products having trypsin inhibitory activity and reduced microbial content, methods of decontaminating such soy products, and compositions containing such soy products. In one preferred embodiment, the legume product is a soy product.

The present invention also relates to the topical application of legume products or compositions containing such legume products for use in the maintenance of healthy skin, nails, and hair as well as the prevention or the treatment of skin, nails, and hair disorders, including, but not limited to: regulating firmness of the skin, hair, or nails; cleansing the skin, hair or nails; reducing and/or delaying hair or nail growth; straightening and/or lightening of hair; treatment and/or prevention of acne; regulating the tone of skin, hair, or nails; regulating the texture of skin, hair, or nails; regulating wrinkles in skin; treatment of external aggressions in skin, hair, or nails; and beautifying the skin, hair, or nails.

Other features and advantages of the present invention will be apparent from the detailed description of the invention and from the claims

DETAILED DESCRIPTION OF THE INVENTION

It is believed that one skilled in the art can, based upon the description herein, utilize the present invention to its fullest extent. The following specific embodiments are to be construed as merely illustrative, and not limitative of the remainder of the disclosure in any way whatsoever.

Unless defined otherwise, all technical and scientific terms used herein have the same meaning as commonly understood by one of ordinary skill in the art to which the invention belongs. Also, all publications, patent applications, patents, and other references mentioned herein are incorporated by reference. As used herein, all percentages are by weight unless otherwise specified.

As used herein, "trypsin inhibitory activity" means the ability of the legume product at a concentration of 0.1% (w/w) to inhibit the activity of the protease trypsin, as measured by the assay set forth below in Example 2. In one embodiment, the legume products of the present invention have a trypsin inhibitory activity of at least about 15%. In a further embodiment, the legume products of the present invention have a trypsin inhibitory activity of at least about 25%, such as at least about 50%.

As used herein, "thiol retention activity" means the ability of the legume product at a concentration of 1%(w/v) to inhibit smoke-induced loss of thiols, as measured by the assay set forth below in Example 3. In one embodiment, the legume products of the present invention have a thiol retention activity of at least about 75%. In a further embodiment, the legume products of the present invention have an thiol retention activity of at least about 90%, such as at least about 95%.

As used herein, "microbial content" means the amount of bacteria, fungi, and yeast present in the legume product. Examples of means to measure microbial content include, but are not limited to, the AOAC 986.23 Method as set forth in "Official Methods of Analysis of AOAC International," edited by Patricia Cunniff, Sixteenth Edition, $5^{th}$ Revision, 1999 (AOAC International) or the USP Method as set forth in "Official Compendia of Standards, USP 24 USP/NF 19", United States Pharmacopeial Convention, Inc., 2000 (Board of Trustees, United States Pharmacopeial Convention, Inc.).

"Objectionable microbial content" means the amount of bacteria, fungi, and yeast present in the legume product that are harmful to humans, including but not limited to coliform, *E. Coli,* Salmonella, thermophilic spores, Bacillus, Enterococcus, Staphylococcus, fecal streptococcus, and those listed in "Disinfection, sterilization, and preservation" 4th edition, Seymour S. Block, pp. 887–888 (1991, Lea & Febiger, Malvern, Pa.).

As used herein, "topical application" means directly laying on or spreading on outer skin using, e.g., by use of the hands or an applicator such as a wipe, puff, roller, or spray.

As used herein, "cosmetically-acceptable" means that the product(s) or compound(s) which the term describes are suitable for use in contact with tissues (e.g., the skin) without undue toxicity, incompatibility, instability, irritation, allergic response, and the like.

As used herein, "topical carrier" means one or more compatible solid or liquid filler diluents that are suitable for topical administration to a mammal. Examples of topical carriers include, but are not limited to, water, waxes, oils, emollients, emulsifiers, thickening agents, gelling agents, and mixtures thereof.

As used herein, "regulating the firmness" means the enhancing of the firmness or elasticity, preventing the loss of firmness or elasticity, or preventing or treating sagging, lax and loose skin, hair, or nails. The firmness or elasticity of the skin can be measured by use of a cutometer. See Handbook of Non-Invasive Methods and the Skin, eds. J. Serup & G. Jemec, Chapter 14.3 (1995). The loss of skin elasticity or firmness may be a result of a number of factors, including but not limited to aging, external aggressions, or the result of an application of a cosmetic to the skin, hair, or nails.

As used herein, "regulating the tone" means the lightening and/or darkening of the appearance of the skin, hair, or nails (e.g., lightening pigmented lesions, darkening skin sallowness, and/or evening the color of the skin).

As used herein, "delaying or reducing nail growth" means the delaying or reducing the growth rate of the nail.

As used herein, "delaying or reducing hair growth" means the delaying or reducing the growth rate of the hair and/or width of hair shaft, including, but not limited to, the reducing the visibility or appearance of hair (e.g., hair on the arms, legs, and face).

As used herein, "cleansing" means the removal of dirt and/or oil from the skin, hair, or nail surface.

As used herein, "regulating the texture" means the smoothing of the surface of the skin, hair, or nail to remove either bumps or crevasses on the surface, including, but mot limited to, smoothing or evening the appearance of the skin.

As used herein, "regulating wrinkles in skin" means preventing, retarding, arresting, or reversing the process of wrinkle or fine line formation in skin, including, but not limited to, reducing the visibility or appearance of wrinkles.

As used herein, "treatment of external aggressions" means the reduction or prevention of the damage from external aggressions in skin, hair, or nails. Examples of external aggressions include, but are not limited to, damage to the skin, hair, and nails from the use or cleansers (e.g., skin and hair cleansers containing surfactants), make-up, and shaving and cutting, as well as environmental damage such as from the UV light (e.g., sun damage from the sunlight or non-natural sources such as UV lamps and solar simulators), ozone, exhaust, pollution, chlorine and compounds containing chlorine, and cigarette smoke. Effects of external aggressions on the skin, nails, and skin include, but are not limited to, oxidative and/or nitrosative damage to and modifications on lipids, carbohydrates, peptides, proteins, nucleic acids, and vitamins. Effects of external aggressions also include, but are not limited to, loss of cell viability, loss or alteration of cell functions, and changes in gene and/or protein expression.

As used herein, "safe and effective amount" means an amount of compound or composition (e.g., the legume product) sufficient to induce a positive modification in the condition to be regulated or treated, but low enough to avoid serious side effects. The safe and effective amount of the compound or composition will vary with the particular condition being treated, the age and physical condition of the end user, the severity of the condition being treated/prevented, the duration of the treatment, the nature of other treatments, the specific compound or product/composition employed, the particular cosmetically-acceptable carrier utilized, and like factors.

Legume Product

What is meant by a "legume product" is a substance derived from a legume fruit. A legume is a plant from the family Leguminosae, which has a dehiscent fruit such as a bean, pea, or lentil. Examples of legumes, include but are not limited to, beans such as soybeans, lentil beans, peas, and peanuts.

The legume product may contain the entire legume fruit (e.g., the legume fruit ground into a powder) or only a portion of the legume (e.g., an extract of the legume). The legume product may be in the form of a fluid (e.g., a mixture of the legume fruit and water) or a solid (e.g., legume fruits powders). When in the form of a fluid, the term "legume product" refers to the solid constituents of the fluid derived from the legume.

The compositions of the present invention comprise a safe and effective amount of the legume product (e.g., soy product). In one embodiment, the composition contains from about 0.001% to about 50%, from about 1% to about 30%, of the legume product (e.g., soy product).

Soy Product

What is meant by a "Soy Product" is a substance derived from the soybean. The soy product may contain only a portion of the soybean (e.g., an extract of the soybean such as a lipid reduced soybean powder or filtered soymilk) or may contain the entire soybean (e.g., a ground powder of the legume). The soy product may be in the form of a fluid (e.g., soymilk) or a solid (e.g., a soybean powder or soymilk powder). When in the form of a fluid, the term "soy product" refers to the solid constituents of the fluid that are derived from the soybean.

In one embodiment, the soy product is soybean powder. Soybean powder may be made by grinding dry soybeans. In one embodiment, the soybean powder has a average particle size of less than about 10 micrometers such as less than about 1 micrometer. In one embodiment, the soybean powder has a moisture content of less than about 10% such as less than about 5%. In one embodiment, the soybean powder is lyophilized.

In one embodiment, the soy product is soymilk or soymilk powder. Soymilk is a combination of solids derived from soybeans and water, the mixture of which has some or all of the insoluble constituents filtered off. Soymilk powder is evaporated soymilk, which in one embodiment, is in a lyophilized or spray-dried form. Procedures for manufacturing soymilk include, but are not limited to, the following three procedures. First, soymilk may be made by placing soybeans into water to allow them to absorb the water. The swelled beans are then ground and additional water is then added. The mixture may then filtered to remove any insoluble residue. Second, soymilk may also be prepared from soybean powder. Soybean powder is thoroughly mixed with water (e.g., for at least one hour), which may then be followed by a filtration process to remove insoluble residues. Third, soymilk can also be reconstituted from soymilk powder by adding water. In one embodiment, soymilk comprises from between about 1% to about 50%, by weight (e.g., from about 5% to about 20%, by weight) of solids from the soybean.

Anti-Microbial Treatment of Legume Product

As discussed above, the surface of legume fruits often contain high levels of microorganisms. Thus, prior to use by humans, the legume product needs to be treated to reduce or eliminate such microorganisms.

In one embodiment, the legume products of the present invention have a total microbial content of less than about 10,000 colony-forming units ("cfu") per gram. In a further embodiment, the soy products of the present invention have a microbial content of less than about 1,000 cfu per gram (such as less than about 100 cfu per gram) of the legume product.

In one embodiment, the legume products of the present invention have a total objectionable microbial content of less than 300 cfu per gram such as less than 150 cfu per gram. In a further embodiment, the legume products of the present invention have an undetectable amount of any objectionable microbials for at least one gram (e.g., at least ten grams) of legume product.

In one embodiment, the legume product is exposed to gamma irradiation. In a further embodiment, the legume product is exposed to between about 2 to about 30 kGy of gamma irradiation, such as between about 5 and about 10 kGy of gamma irradiation. Applicants have unexpectedly found that such treatment reduces the microbial content of the legume product, while maintaining its biological activity (e.g., serine protease inhibitory activity). Applicants have also found that treatment of legume products with gamma irradiation maintains the cosmetic elegance of the legume product, such as maintained its natural colors and did not induce significant malodors.

Other anti-microbial processes that also maintain the protease inhibitory activity of the legume product that can be practiced alone or in combination with gamma irradiation, include, but are not limited to, exposure to x-rays, high energy electron or proton beams, ultraviolet radiation, hydrostatic pressure, and addition of chemical agents possessing antimicrobial activity, and combinations thereof. A complete list of methods for microbial content reduction is set forth in "Disinfection, sterilization, and preservation" 4th edition, Seymour S. Block, pp. 887–888 (1991, Lea & Febiger, Malvern, Pa.).

Applicants have found that processes using thermal treatment may result in a substantial loss in protease inhibitory activity and, thus, should be used with caution. For example, applicants have found that heating soymilk to 100° C. for only 10 minutes reduced the trypsin inhibitory activity of the soymilk from 86% (when maintained at 4° C.) to 46%. Applicants have found that heating soymilk can also result in a change of the color or odor of the soybean product.

Topical Compositions

The topical compositions useful in the present invention involve formulations suitable for topical application to skin. In one embodiment, the composition comprises the soy product and a cosmetically-acceptable topical carrier. In one embodiment, the cosmetically-acceptable topical carrier is from about 50% to abut 99.99%, by weight, of the composition (e.g., from about 80% to about 95%, by weight, of the composition.

The compositions may be made into a wide variety of product types that include but are not limited to lotions, creams, gels, sticks, sprays, shaving creams, ointments, cleansing liquid washes and solid bars, shampoos, pastes, powders, mousses, shaving creams, wipes, patches, nail lacquers, wound dressing and adhesive bandages, hydrogels, films and make-up such as foundations, mascaras, and lipsticks. These product types may comprise several types of cosmetically acceptable topical carriers including, but not limited to solutions, emulsions (e.g., microemulsions and nanoemulsions), gels, solids and liposomes. The following are non-limitative examples of such carriers. Other carriers can be formulated by those of ordinary skill in the art.

The topical compositions useful in the present invention can be formulated as solutions. Solutions typically include an aqueous solvent (e.g., from about 50% to about 99.99% or from about 90% to about 99% of a cosmetically acceptable aqueous solvent).

Topical compositions useful in the subject invention may be formulated as a solution comprising an emollient. Such compositions preferably contain from about 2% to about 50% of an emollient(s). As used herein, "emollients" refer to materials used for the prevention or relief of dryness, as well as for the protection of the skin. A wide variety of suitable emollients are known and may be used herein. Sagarin, Cosmetics, Science and Technology, 2nd Edition, Vol. 1, pp. 32–43 (1972) and the International Cosmetic Ingredient Dictionary and Handbook, eds. Wenninger and McEwen, pp. 1656–61, 1626, and 1654–55 (The Cosmetic, Toiletry, and Fragrance Assoc., Washington, D.C., $7^{th}$ Edition, 1997) (hereinafter "ICI Handbook") contains numerous examples of suitable materials.

A lotion can be made from such a solution. Lotions typically comprise from about 1% to about 20% (e.g., from about 5% to about 10%) of an emollient(s) and from about 50% to about 90% (e.g., from about 60% to about 80%) of water.

Another type of product that may be formulated from a solution is a cream. A cream typically comprises from about 5% to about 50% (e.g., from about 10% to about 20%) of an emollient(s) and from about 45% to about 85% (e.g., from about 50% to about 75%) of water.

Yet another type of product that may be formulated from a solution is an ointment. An ointment may comprise a simple base of animal or vegetable oils or semi-solid hydrocarbons. An ointment may comprise from about 2% to about 10% of an emollient(s) plus from about 0.1% to about 2% of a thickening agent(s). A more complete disclosure of thickening agents or viscosity increasing agents useful herein can be found in Sagarin, Cosmetics, Science and Technology, 2nd Edition, Vol. 1, pp. 72–73 (1972) and the ICI Handbook pp. 1693–1697.

The topical compositions useful in the present invention formulated as emulsions. If the carrier is an emulsion, from about 1% to about 10% (e.g., from about 2% to about 5%) of the carrier comprises an emulsifier(s). Emulsifiers may be nonionic, anionic or cationic. Suitable emulsifiers are disclosed in, for example, U.S. Pat. Nos. 3,755,560, 4,421,769, McCutcheon's Detergents and Emulsifiers, North American Edition, pp. 317–324 (1986), and the ICI Handbook, pp.1673–1686.

Lotions and creams can be formulated as emulsions. Typically such lotions comprise from 0.5% to about 5% of an emulsifier(s). Such creams would typically comprise from about 1% to about 20% (e.g., from about 5% to about 10%) of an emollient(s); from about 20% to about 80% (e.g., from 30% to about 70%) of water; and from about 1% to about 10% (e.g., from about 2% to about 5%) of an emulsifier(s).

Single emulsion skin care preparations, such as lotions and creams, of the oil-in-water type and water-in-oil type are well-known in the cosmetic art and are useful in the subject invention. Multiphase emulsion compositions, such as the water-in-oil-in-water type, as disclosed in U.S. Pat. Nos. 4,254,105 and 4,960,764, are also useful in the subject invention. In general, such single or multiphase emulsions contain water, emollients, and emulsifiers as essential ingredients.

The topical compositions of this invention can also be formulated as a gel (e.g., an aqueous gel using a suitable gelling agent(s)). Suitable gelling agents for aqueous gels include, but are not limited to, natural gums, acrylic acid and acrylate polymers and copolymers, and cellulose derivatives (e.g., hydroxymethyl cellulose and hydroxypropyl cellulose). Suitable gelling agents for oils (such as mineral oil) include, but are not limited to, hydrogenated butylene/ethylene/styrene copolymer and hydrogenated ethylene/propylene/styrene copolymer. Such gels typically comprises between about 0.1% and 5%, by weight, of such gelling agents.

The topical compositions of the present invention can also be formulated into a solid formulation (e.g., a wax-based stick, soap bar composition, powder, or a wipe containing powder).

Liposomal formulations are also useful compositions of the subject invention. Examples of liposomes are unilamellar, multilamellar, and paucilamellar liposomes, which may or may not contain phospholipids. Such compositions can be prepared by first combining hesperetin with a phospholipid, such as dipalmitoylphosphatidyl choline, cholesterol and water according to the method described in Mezei & Gulasekharam, "Liposomes—A Selective Drug Delivery System for the Topical Route of Administration; Gel Dosage Form", Journal of Pharmaceutics and Pharmacology, Vol. 34 (1982), pp. 473–474, or a modification thereof. Epidermal lipids of suitable composition for forming liposomes may be substituted for the phospholipid. The liposome preparation may then incorporated into one of the above carriers (e.g., a gel or an oil-in-water emulsion) in order to produce the liposomal formulation. Other compositions and pharmaceutical uses of topically applied liposomes are described in Mezei, M., "Liposomes as a Skin Drug Delivery System", Topics in Pharmaceutical Sciences (D. D. Breimer and P. Speiser, eds.,), Elsevier Science Publishers B. V., New York, N.Y., 1985, pp. 345–358, PCT Patent Application No. WO96/31194 and U.S. Pat. No. 5,260,065.

The topical compositions useful in the subject invention may contain, in addition to the aforementioned components, a wide variety of additional oil-soluble materials and/or water-soluble materials conventionally used in compositions for use on skin, hair, and nails at their art-established levels.

Additional Cosmetically Active Agents

In one embodiment, the topical composition further comprises another cosmetically active agent in addition to the legume product. What is meant by a "cosmetically active agent" is a compound that has a cosmetic or therapeutic effect on the skin, hair, or nails, e.g., lightening agents, darkening agents such as self-tanning agents, anti-acne agents, shine control agents, anti-microbial agents, anti-inflammatory agents, anti-mycotic agents, anti-parasite agents, external analgesics, sunscreens, photoprotectors, antioxidants, keratolytic agents, detergents/surfactants, moisturizers, nutrients, vitamins, energy enhancers, anti-perspiration agents, astringents, deodorants, hair removers, firming agents, anti-callous agents, and agents for hair, nail, and/or skin conditioning.

In one embodiment, the agent is selected from, but not limited to, the group consisting of hydroxy acids, benzoyl peroxide, sulfur resorcinol, ascorbic acid, D-panthenol, hydroquinone, octyl methoxycinnimate, titanium dioxide, octyl salicylate, homosalate, avobenzone, polyphenolics, carotenoids, free radical scavengers, spin traps, retinoids such as retinol and retinyl palmitate, ceramides, polyunsaturated fatty acids, essential fatty acids, enzymes, enzyme inhibitors, minerals, hormones such as estrogens, steroids such as hydrocortisone, 2-dimethylaminoethanol, copper salts such as copper chloride, peptides containing copper such as Cu:Gly-His-Lys, coenzyme Q10, peptides such as those disclosed in PCT Patent Application WO00/15188, lipoic acid, amino acids such a proline and tyrosine, vitamins, lactobionic acid, acetyl-coenzyme A, niacin, riboflavin, thiamin, ribose, electron transporters such as NADH and FADH2, and other botanical extracts such as aloe vera, and derivatives and mixtures thereof. The cosmetically active agent will typically be present in the composition of the invention in an amount of from about 0.001% to about 20% by weight of the composition, e.g., about 0.01% to about 10% such as about 0.1% to about 5%.

Examples of vitamins include, but are not limited to, vitamin A, vitamin Bs such as vitamin B3, vitamin B5, and vitamin B12, vitamin C, vitamin K, and vitamin E and derivatives thereof.

Examples of hydroxy acids include, but are not limited to, glycolic acid, lactic acid, malic acid, salicylic acid, citric acid, and tartaric acid. See, e.g., European Patent Application No. 273,202. Examples of antioxidants include, but are not limited to, water-soluble antioxidants such as sulfhydryl compounds and their derivatives (e.g., sodium metabisulfite and N-acetyl-cysteine), lipoic acid and dihydrolipoic acid, resveratrol, lactoferrin, and ascorbic acid and ascorbic acid derivatives (e.g., ascorbyl palmitate and ascorbyl polypeptide). Oil-soluble antioxidants suitable for use in the compositions of this invention include, but are not limited to, butylated hydroxytoluene, retinoids (e.g., retinol and retinyl palmitate), tocopherols (e.g., tocopherol acetate), tocotrienols, and ubiquinone. Natural extracts containing antioxidants suitable for use in the compositions of this invention, include, but not limited to, extracts containing flavonoids and isoflavonoids and their derivatives (e.g., genistein and diadzein), extracts containing resveratrol and the like. Examples of such natural extracts include grape seed, green tea, pine bark, and propolis. Other examples of antioxidants may be found on pages 1612–13 of the ICI Handbook.

Other Materials

Various other materials may also be present in the compositions useful in the subject invention. These include humectants, proteins and polypeptides, preservatives and an alkaline agent. Examples of such agents are disclosed in the ICI Handbook, pp.1650–1667. The compositions of the present invention may also comprise chelating agents (e.g., EDTA) and preservatives (e.g., parabens). Examples of suitable preservatives and chelating agents are listed in pp. 1626 and 1654–55 of the ICI Handbook. In addition, the topical compositions useful herein can contain conventional cosmetic adjuvants, such as dyes, opacifiers (e.g., titanium dioxide), pigments, and fragrances.

Mineral Water

The legume product (e.g., soymilk) and compositions of the present invention may be prepared using a mineral water. In one embodiment, the mineral water has a mineralization of at least about 200 mg/L (e.g., from about 300 mg/L to about 1000 mg/L). In one embodiment, the mineral water comprises at least about 10 mg/L of calcium and/or at least about 5 mg/L of magnesium.

EXAMPLE 1

Gamma Irradiation of Legume Product

Applicants have found that soymilk powder prior to any antimicrobial processing such as gamma irradiation has high levels microbial content, ranging from up to 50,000 cfu per gram. Such products were also found to have detectable levels of objectionable microbial content, such as fecal streptococci, at levels up to 20,000 cfu per gram.

Applicants have exposed various amounts (e.g., from about 1 g to about 200 kg) of soymilk powder to gamma irradiation varying from 1 kGy to 16 kGy. The dose or gamma irradiation needed for a reduction a total microbial content to less than about 100 cfu per gram was found to be about 10 kGy. The dose for one log reduction for fecal streptococci is determined to be about 3 kGy and a dose of about 5 kGy was found to consistently reduce this microbial content within a 10 gram sample of soymilk powder to undetectable levels. However, the amount of gamma irradiation used on the legume product will ultimately be determined by the microbial content and size of the soy product to be so treated.

EXAMPLE 2

Trypsin Inhibitory Activity of Legume Product

The inhibition of trypsin-induced cleavage of a fluorescent casein peptide was measured using the EnzChek™ protease assay kit, following manufacturer's instructions (EnzChek™ Protease Assay Kits Product Information, Revised Mar. 15, 1999; Molecular Probes, Eugene Oreg.). In summary, various soy preparations were first diluted in 1× digestion buffer (provided in kit) and incubated at different concentrations with 1000 units of trypsin (Sigma, St. Louis, Mo.) dissolved in 1× digestion buffer. A pure serine protease inhibitor (soybean trypsin inhibitor, from Sigma, St. Louis, Mo.) was used as a positive control at 0.1, 0.01%, and 0.001% w/v. Then, 1.0 mg/ml stock solution of BODIPY FL casein was prepared by adding 0.2 mL of deionized water to the vials supplied with this substrate (provided in kit), then made to a final working concentration of 10 microgram/ml in digestion buffer. Following incubation of the trypsin, with or without the test material, with the BODIPY fluorescent casein substrate at room temperature for one hour, fluorescence was measured (excitation 485 nm/emission 530 nm) on a SpectraMax® Gemini microtiter plate reader (Molecular Devices Corporation, Sunnyvale, Calif.) using Softmax® Pro 3.0 software (Molecular Devices Corporation). Each experiment was performed in three replicates and was repeated twice.

This assay was performed on soy products processed seven different ways. Example A was soybeans ground into powder (Sunlight Foods Corporation, Taipei County, Taiwan, R.O.C.). Example B was soybean powder of Example A exposed to about 8–15 kGy of gamma irradiation. Example C was soybean powder in which the oil in the soybean powder was removed by extraction (Soyafluff® 200W from Central Soya Company, Inc., Fort Weyne, Ind.). Example D was soymilk powder made with dehulled soybeans and water that was subsequently filtered and heated and spray dried (Devansoy Farms, Carroll, Iowa) and exposed to between about 7–9 kGy of gamma irradiation. Example E was soymilk powder obtained by mixing soy beans and water, heating the mixture overnight, and adding 1,3-butylene glycol to the mixture (Flavosterone SB from Ichimaru Pharcos Co., Ltd, Gifu Japan). Example F was soymilk powder obtained by mixing soy beans and water, heating the mixture overnight, and subsequently adding ethanol to the mixture (Flavosterone SE from Ichimaru Pharcos Co., Ltd, Gifu Japan). Example G was an extract of soy proteins (Vegeseryl HGP LS 8572 from Laboratories Serobiologiques S.A., Pulnoy, France). These soy products were compared to Soy Trypsin Inhibitor (STI) (Sigma).

The percent inhibition of trypsin cleavage of the substrate by the different soy preparations was calculated using Microsoft Excel™ and is reported in Table 1.

TABLE 1

| Tested Product | Concentration | % Inhibition of Trypsin |
|---|---|---|
| STI | 0.01 | 43.0 |
| STI | 0.1 | 76.1 |
| Example A | 0.01 | 32.8 |
| Example A | 0.1 | 67.1 |
| Example B | 0.01 | 31.5 |
| Example B | 0.1 | 67.2 |
| Example C | 0.01 | 22.7 |
| Example C | 0.1 | 36.2 |
| Example D | 0.01 | 8.92 |
| Example D | 0.1 | 17.4 |
| Example E | 0.01 | 7.83 |
| Example E | 0.1 | 10.8 |
| Example F | 0.01 | 4.87 |
| Example F | 0.1 | 5.99 |
| Example G | 0.1 | 6.85 |

As shown in Table 1, STI can inhibit trypsin-induced cleavage in a dose response manner. Example A, which is soybean powder, also significantly inhibited trypsin activity. Further gamma irradiation of the soybean powder (i.e., Example B), while reducing the microbial content of the soybean powder, unexpectedly did not significantly impact the trypsin inhibition activity of the soybean powder. The heat and/or extraction processing of Examples C–G, however, did significantly reduce the trypsin inhibitory activity of the soybean powder.

EXAMPLE 3

Thiol Retention Activity of Legume Product

The ability of soy powder to prevent smoke-induced loss of thiols was evaluated in normal human dermal fibroblasts (Clonetics, San Diego, Calif.). Thiols, chiefly glutathione, are part of the endogenous cellular antioxidant defense system. Glutathione serves as a redox buffer, thereby, maintaining the balance between oxidants and antioxidants. Glutathione is also the preferred substrate for several enzymes such as the glutathione peroxidases (decomposing peroxides) and the glutathione-S-transferases (a major group of detoxification enzymes). See, A. Meister, Cancer Res. 54:1969s–1975s (1994).

Cutaneous antioxidants (both enzymatic and non-enzymatic), including glutathione, are depleted after UV or ozone exposure. See, M. J. Connor and L. A. Wheeler, Photochem. Photobiol. 46:239–246 (1987) and R. M. Tyrrell and M. Pidoux, Photochem. Photobiol. 47:405–412 (1988). In cell culture models, low intracellular glutathione (GSH) levels lead to a higher UV radiation sensitivity. Topical application of cysteine derivatives on rat skin has been shown to protect against UV radiation-induced photodamage; this benefit was correlated with an increase in GSH synthesis. See, L. T. van den Broeke and G. M. J. Beijersbergen van Henegouwen, J. Photochem. Photobiol. B Biol. 27:61–65 (1995); K. Hanada, et al., J. Invest. Dermatol. 108:727–730 (1997); and D. P. T. Steenvoorden, et al., Photochem Photobiol. 67:651–656 (1998). Consequently, glucothione is a major endogenous antioxidant, highly responsive against environmental challenges, able to regulate the tone and the wrinkling of skin, as well as treat external aggression.

In this experiment, normal human neonatal dermal fibroblasts seeded in 24-well format Transwell inserts (Corning Costar, Cambridge, Mass.) were incubated with media containing various concentrations of soymilk powder (gamma irradiated at about 5 kGy) for 24 hours prior to exposure with either placebo (mock) or cigarette smoke (1 cigarette, BASIC Full Flavor 100's cigarettes, Philip Morris, Richmond, Va.) for 10 minutes. Prior to smoke exposure, the medium above the inserts containing the soy product was removed, and the cells were washed 3 times with Dulbecco's Phosphate-Buffered Saline (Life Technologies, Gaithersburg, Md.) before being smoke-exposed with only media below the inserts. Immediately after exposure, the cells were incubated for another 24-hour period with the previous medium. The cells were washed again, 5 times with Dulbecco's Phosphate-Buffered Saline, and intracellular thiols were then measured by adding 60 μM monobromobimane (Molecular Probes, Eugene, Oreg., USA) to the cells and incubating at 37° C. for 30 minutes before the fluorescence reading. In the presence of thiols, the monobromobimane becomes fluorescent. This fluorescence was measured using a CytoFluor® Fluorescence Plate Reader (PerSeptive Biosystems, Framingham, Mass., USA) set with the following filter combination: excitation at 360 nm and emission at 460 nm.

The results of this experiment are set-forth in Table 2.

TABLE 2

| | Soymilk Powder concentration (weight %) | Thiols (Percent of Thiols contained in No Smoke Group; Mean ± S.E.M.) |
|---|---|---|
| No Smoke | 0 | 100 ± 6.71 |
| Smoke (10 min.) | 0 | 65.38 ± 7.16 |
| | 0.5 | 91.24 ± 14.25 |
| | 1 | 95.39 ± 4.52 |
| | 2 | 106.92 ± 17.06 |

These results indicate that gamma irradiated soymilk powder surprisingly afforded a protection against smoke-induced loss of thiols (data represent the mean +Standard of the mean of replicates from 3 independent experiments).

It is understood that while the invention has been described in conjunction with the detailed description thereof, that the foregoing description is intended to illustrate and not limit the scope of the invention, which is defined by the scope of the appended claims. Other aspects, advantages, and modifications are within the claims.

What is claimed is:

1. A soy product having:
   (a) a trypsin inhibitory activity of at least about 15%; and
   (b) a microbial content less than about 1000 cfu per gram, wherein said soy product is a powder having a particle size less than about 10 micrometers.

2. A soy product of claim 1, said soy product having an objectionable microbial content less than about 150 cfu per gram.

3. A soy product of claim 1, said soy product having no detectable objectionable microbial content per gram.

4. A soy product having:
   (a) a trypsin inhibitory activity of at least about 50%; and
   (b) a microbial content less than about 10,000 cfu per gram, wherein said soy product is a powder having a particle size less than about 10 micrometers.

5. A soy product of claim 4, said soy product further having an objectionable microbial content less than about 150 cfu per gram.

6. A soy product of claim 5, said soy product having a microbial content of less than about 1000 cfu per gram.

7. A soy product of claim 6, said soy product having no detectable objectionable microbial content per gram.

8. A soy product of claim 1, wherein said soy product has a thiol retention activity of at least about 75%.

9. A soy product of claim 4, wherein said soy product has a thiol retention activity of at least about 75%.

10. A soy product of claim 1, wherein said soy product has been exposed to gamma irradiation.

11. A soy product of claim 3, wherein said soy product has been exposed to gamma irradiation.

12. A soy product of claim 4, wherein said soy product has been exposed to gamma irradiation.

13. A soy product of claim 7, wherein said soy product has been exposed to gamma irradiation.

14. A soy product of claim 10, wherein said soy product has been exposed to about 5 to about 16 kGy gamma irradiation.

15. A soy product of claim 11, wherein said soy product has been exposed to about 5 to about 16 kGy gamma irradiation.

16. A soy product of claim 12, wherein said soy product has been exposed to about 5 to about 16 kGy gamma irradiation.

17. A soy product of claim 13, wherein said soy product has been exposed to about 5 to about 16 kGy gamma irradiation.

18. A soy product of claim 1, wherein said soy product is soymilk powder.

19. A soy product of claim 1, wherein said soy product is soybean powder.

20. A soy product of claim 4, wherein said soy product is soymilk powder.

21. A soy product of claim 4, wherein said soy product is soybean powder.

22. A soy product of claim 10, wherein said soy product is soymilk powder.

23. A soy product of claim 10, wherein said soy product is soybean powder.

24. A soy product of claim 12, wherein said soy product is soymilk powder.

25. A soy product of claim 12, wherein said soy product is soybean powder.

* * * * *